United States Patent
Massick

(10) Patent No.: US 7,790,467 B1
(45) Date of Patent: Sep. 7, 2010

(54) DIODE LASER BASED KETONE AND ALDEHYDE DETECTION

(75) Inventor: Steven Michael Massick, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 27 days.

(21) Appl. No.: 11/849,750

(22) Filed: Sep. 4, 2007

Related U.S. Application Data

(60) Provisional application No. 60/824,361, filed on Sep. 1, 2006.

(51) Int. Cl.
*G01N 33/00* (2006.01)
*G01N 31/00* (2006.01)

(52) U.S. Cl. .................. 436/130; 600/529; 600/532; 73/23.3; 356/37; 250/339.13

(58) Field of Classification Search ................ 436/130; 600/529, 532; 73/23.3; 356/37; 250/339.13
See application file for complete search history.

(56) References Cited

U.S. PATENT DOCUMENTS

| | | | |
|---|---|---|---|
| 895,497 A * | 8/1908 | Barzana et al. ............ 451/352 |
| 5,112,741 A * | 5/1992 | Palmer et al. ................ 435/25 |
| 5,174,959 A * | 12/1992 | Kundu et al. ................. 422/59 |
| 5,425,374 A | 6/1995 | Ueda et al. |
| 5,754,288 A | 5/1998 | Yamamoto et al. |
| 6,319,724 B1 | 11/2001 | Lewis et al. |
| 6,363,772 B1 | 4/2002 | Berry |
| 6,454,723 B1 | 9/2002 | Montagnino |
| 6,540,691 B1 | 4/2003 | Phillips |
| 7,052,854 B2 | 5/2006 | Melker et al. |
| 7,076,371 B2 | 7/2006 | Fu |
| 7,300,408 B2 * | 11/2007 | Hancock et al. ............. 600/532 |
| 2006/0105464 A1 * | 5/2006 | Weber et al. ................ 436/128 |

OTHER PUBLICATIONS

Tsai, S., & Que Hee, S.S., A New Passive Sampler for Regulated Workplace Ketones. AIHAJ.2000:61,(808-814).*

Cao, Wenqing et al., "Breath Analysis: Potential for Clinical Diagnosis and Exposure Assessment", *Clinical Chemistry* vol. 52, No. 5 2006, 800-811.

Grote, Christoph et al., "Solid-Phase Microextraction for the Analysis of Human Breath", *Analytical Chemistry* vol. 69, No. 4, American Chemical Society Feb. 15, 1997, 587-596.

Koziel, Jacek A. et al., "Field Sampling and Determination of Formaldehyde in Indoor Air with Solid-Phase Microextraction and On-Fiber Derivatization", *Environmental Science & Technology* vol. 35, No. 7 2001, 1481-1486.

(Continued)

*Primary Examiner*—Vickie Kim
*Assistant Examiner*—Rebecca Fritchman
(74) *Attorney, Agent, or Firm*—Jeffrey D. Myers; Samantha A. Updegraff; Peacock Myers, P.C.

(57) ABSTRACT

An apparatus and method for quantifying ketone or alydehyde concentrations of gas. The invention includes passing a gas sample through a reactor and an optical cell and determining a concentration of a gaseous reaction product. Using the concentration of the gaseous reaction product and a predetermined reaction conversion efficiency, a ketone or aldehyde concentration is calculated. This invention can be used for diabetes screening, diabetes maintenance, identification and quantification of ketosis, explosives detection and formaldehyde detection.

14 Claims, 4 Drawing Sheets

OTHER PUBLICATIONS

Likhodii, Sergei S. et al., "Breath Acetone as a Measure of Systemic Ketosis Assessed in a Rat Model of the Ketogenic Diet", *Clinical Chemistry* vol. 48, No. 1 2002, 115-120.

Lord, Heather et al., "Breath Analysis and Monitoring by Membrane Extraction with Sorbent Interface", *Analytical Chemistry* vol. 74, No. 21, American Chemical Society Nov. 1, 2002, 5650-5657.

Martos, Perry A. et al., "Sampling and Determination of Formaldehyde Using Solid-Phase Microextraction with On-Fiber Derivatization", *Analytical Chemistry* vol. 70, No. 11, American Chemical Society Jun. 1, 1998, 2311-2320.

Massick, Steve M. et al., "Breath Acetone Detection", *Optical Methods in the Life Sciences, Proceedings of the SPIE* vol. 6386 2006.

Musa-Veloso, Kathy et al., "Breath acetone is a reliable indicator of ketosis in adulsts consuming ketogenic meals", *Am J Clin Nutr* vol. 76, American Society for Clinical Nutrition 2002, 65-70.

Phillips, Michael et al., "Detection of endogenous acetone in normal human breath", *Journal of Chromatography* vol. 422, Elsevier Science Publishers, Amsterdam, The Netherlands 1987, 235-238.

Phillips, Michael et al., "Method for the Collection and Assay of Volatile Organic Compounds in Breath", *Analytical Biochemistry* vol. 247, Academic Press 1997, 272-278.

Smith, David et al., "Trace gases in breath of healthy volunteers when fasting and after a protein-calorie meal: a preliminary study", *Journal of Applied Physiology* vol. 87, No. 5, American Physiological Society 1999, 1584-1588.

Trotter, M. D. et al., "The Rapid Determination of Acetone in Breath and Plasma", *Clinica Chimica Acta* vol. 35 1971, 137-143.

Tsai, Shih-Wei et al., "A New Passive Sampler for Aldehydes", *AIHA Journal, abstract only* vol. 60, Issue 4, American Industrial Hygiene Association Jul. 1999, 463-473.

Tsai, Shih-Wei et al., "A New Passive Sampler for Regulated Workplace Ketones", *AIHA Journal, abstract only* vol. 61, Issue 6, American Industrial Hygiene Association Jan. 2000, 808-814.

Wang, Chuji et al., "Measurements of Cavity Ringdown Spectroscopy of Acetone in the Ultraviolet and Near-Infrared Spectral Regions: Potential for Development of a Breath Analyzer", *Applied Spectroscopy* vol. 58, No. 7, Society for Applied Spectroscopy 2004, 784-791.

Yamane, Norio et al., "Relationship between skin acetone and blood B-hydroxybutyrate concentrations in diabetes", *Clinica Chimica Acta* vol. 365, Elsevier, B.V. 2006, 325-329.

Barnett, D. et al., "Breath Acetone and Blood Sugar Measurements in Diabetes", *Clinical Science* vol. 37 1969, 570.

Crofford, O. B. et al., "Acetone in breath and blood", *Trans Am Clin Climatol* vol. 88 1977, 128-139.

Henderson, M. J. et al., "Acetone in the breath: a study of acetone exhalation in diabetic and nondiabetic human subjects", *Diabetes* vol. 1 1952, 188-193.

Levey, S. et al., "Studies of Metabolic Products in Expired Air. II. Acetone", *Journal of Laboratory and Clinical Medicine* vol. 63 1964, 574-584.

Rooth, G. et al., "Acetone in Alveolar Air and Control of Diabetes", *Lancet* vol. 2 1966, 1102-1105.

\* cited by examiner

DIODE LASER BASED KETONE AND ALDEHYDE DETECTION

CROSS-REFERENCE TO RELATED APPLICATIONS

This application claims priority to and the benefit of the filing of U.S. Provisional Patent Application Ser. No. 60/824,361, entitled "Diode Laser Based Ketone and Aldehyde Detection", filed on Sep. 1, 2006, and the specification thereof is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of U.S. Army Medical Research Acquisition Activity DAMD17-03-C-0032.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to methods and apparatuses for ketone and aldehyde detection, particularly in human and animal breath.

2. Description of Related Art

The present invention solves known problems in ketone and aldehyde vapor detection by means of a chemical reaction with powders, films, or solids of hydrogen halide adducts of hydroxylamines, or modified hydroxylamines. The reaction forms two products: an oxime and a hydrogen halide, e.g. hydrogen fluoride, hydrogen chloride, hydrogen bromide, or hydrogen iodide. Previous embodiments of aldehyde and ketone detection by reaction with solid hydroxylamines have quantified the oxime product by gas chromatographic or gas chromatographic-mass spectrometric methods.

The present invention quantifies aldehydes and/or ketones by the optical detection of the hydrogen halide gas released from the reaction of aldehydes or ketones with hydroxylamine hydrogen halides. The invention is efficacious with hydroxylamine hydrochlorides, but is not limited to hydrochlorides. This invention is applicable to breath acetone analysis for diabetes screening, diabetes maintenance, exercise physiology, and identification and quantification of ketosis in humans and animals; explosives detection, e.g. triacetone triperoxide (TATP); formaldehyde detection; and all types of gas sensing applications targeting aldehydes or ketones.

U.S. Patents bearing a relation to the present invention include U.S. Pat. Nos. 7,076,371; 7,052,854; 7,052,854; 6,319,724; 6,363,772; 6,454,723; 6,540,691; 5,174,959; 5,425,374; and 5,754,288.

BRIEF SUMMARY OF THE INVENTION

The present invention provides a method of quantifying ketone or aldehyde concentrations in a gas. The method preferably includes the steps of passing a gas sample through a reactor comprising a chemisorbent material that reacts with ketones or aldehydes into an optical cell. Then employing spectroscopy of the contents of the optical cell to determine the concentration of a gaseous reaction product and calculating the ketone or aldehyde concentration from the concentration of the gaseous reaction product and a predetermined reaction conversion efficiency. The gas preferably passes through a desiccant, and the ketones or aldehydes are preferably acetone or formaldehyde.

The chemisorbent material is one or more hydroxylamine hydrogen halides selected from a group of hydrogen halide adducts of hydroxylamine (HA), modified HA materials with oxygen bound substituents, or modified HA materials with nitrogen bound substituents. The conversion efficiency mentioned above is determined by measuring the gaseous reaction product concentration of an acetone sample of known concentration. The step of employing spectroscopy is done using a diode laser spectroscopy method where the diode laser detects hydrogen chloride gas (HCl) at an overtone vibrational transition preferably at approximately 1742.4 nm. This method is employed to test for diabetes screening, diabetes maintenance, identification and quantification of ketosis, explosives detection, and formaldehyde detection.

The invention also provides an apparatus for quantifying ketone or aldehyde concentrations in gas. The apparatus includes a gas sample that passes through a reactor into an optical cell, wherein the reactor comprises a chemisorbent material that reacts with ketones or aldehydes. The apparatus also includes a spectroscopy device for measuring the contents of the optical cell to determine a concentration of a gaseous reaction product and includes a device for calculating the ketone or aldehyde concentration from the concentration of the gaseous reaction product and a predetermined reaction conversion efficiency. The ketones or aldehydes can be acetone or formaldyhyde, and the chemisorbent material is one or more hydroxylamine hydrogen halides. The hydroxylamine hydrogen halides are chosen from a group of hydrogen halide adducts of hydroxylamine (HA), modified HA materials with oxygen bound substituents or modified HA materials with nitrogen bound substituents.

The apparatus includes two desiccants. The first desiccant traps water only, not the aldehyde or ketone. The second desiccant traps both water and the ketone or aldehyde. This second desiccant is used for determining a correction for the variable oxygen content of expired air and is only necessary for highly accurate measurements. The spectroscopy device discussed above is a diode laser that detects HCl at an overtone vibrational transition. The laser diode preferably detects HCl at approximately 1742.4 nm.

The apparatus of this invention is employed to test for one or more of the items selected from a group consisting of diabetes screening, diabetes maintenance, identification and quantification of ketosis, exercise physiology, nutritional studies, explosives detection, and formaldehyde detection.

An object of the present invention is to provide optical detection of ketones and/or aldehydes.

Another objection of the present invention is to provide breath acetone analysis for diabetes screening, diabetes maintenance, and identification and quantification of ketosis in humans and animals, exercise physiology, nutritional studies, explosives detection, formaldehyde detection and all types of gas sensing applications targeting aldehydes and ketones.

An advantage of the present invention is that it can be reduced to practice in a portable, battery-operated design that can provide rapid measurements of ketone or aldehyde concentrations. The chemical conversion of the ketone or aldehyde to an easily detected gaseous species, e.g. HCl, permits the use of commercially available, robust near infrared diode lasers and detectors. Gas chromatographic and gas chromatographic-mass spectrometric methods are not required.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of a method and apparatus for breath acetone detection that utilizes a gas-solid chemical reaction of acetone that releases a reaction product that is easily detected by optical methods (preferably diode laser based). The scope of the invention is not limited to acetone detection in that the method is applicable to any aldehyde or ketone, for example formaldehyde detection. The technique is particularly appropriate for diabetes screening and diabetes maintenance. Acetone is good marker of metabolic stress as it has distinct chemical reactivity and is volatile enough to be detected rapidly through simple exhalation, provided that a sufficiently sensitive and economical probe of acetone is available. An undiagnosed Type I and Type II diabetic will have elevated breath acetone levels.

Figure 1:
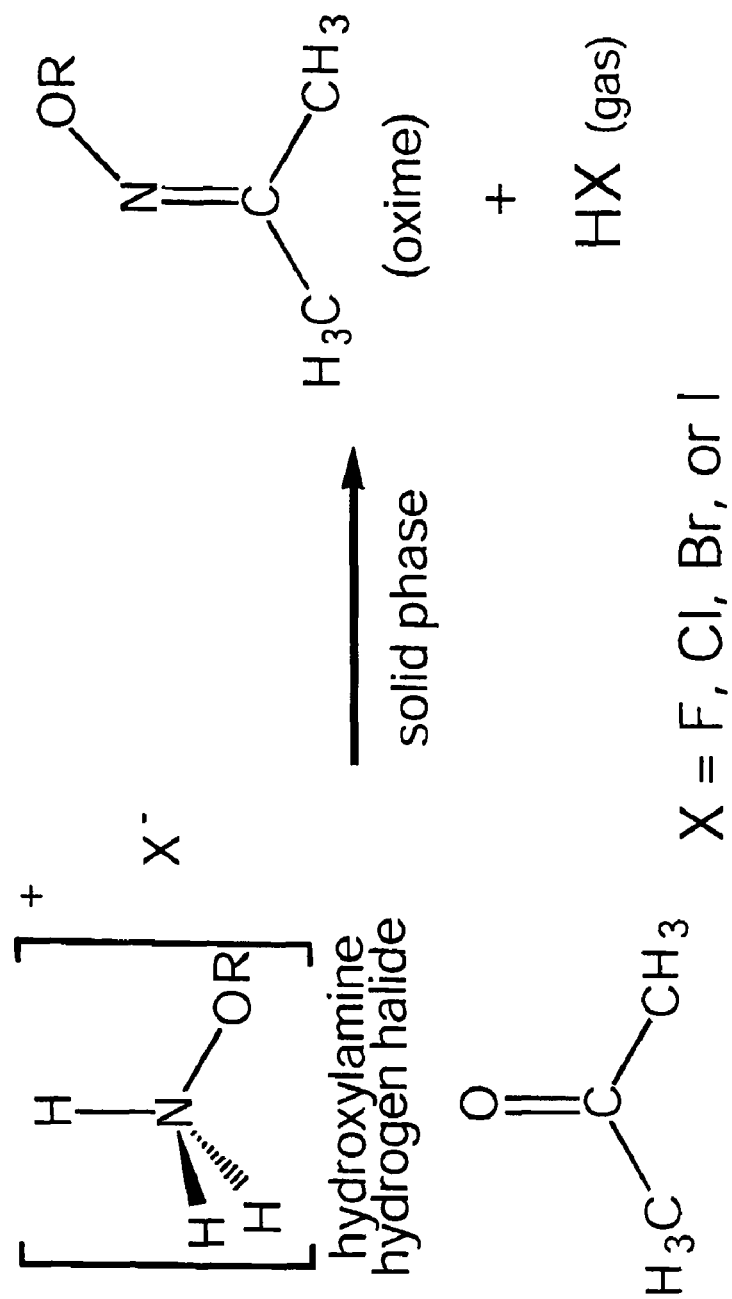
FIG. 1 illustrates the ketone/aldehyde chemical reaction resulting in gaseous HCl release from a hydroxylamine hydrochloride solid.

The key transduction event is the chemical reaction specific to aldehydes and ketones that converts the relatively near infrared (NIR) transparent acetone into hydrochloric acid (HCl), which is a much more intense absorber at the wavelengths accessible by room temperature diode lasers. The chemical conversion is based on a laboratory technique used to quantify aldehydes or ketones by reaction with hydroxylamine hydrochlorides. FIG. 1 illustrates the chemical reaction. The reaction products are HCl and an oxime Schiff base adduct of the aldehyde or ketone. Previous examples of ketone measurements by reaction with hydroxylamines use solution phase pH changes (aqueous HCl) or subsequent quantification of the oxime product by gas chromatography/mass spectrometry to calculate the ketone concentration. The present method directly detects gaseous HCl emitted from a gas solid reaction of acetone with solid hydroxylamine hydrochlorides. This chemical conversion technique can also be implemented with the hydrogen fluoride, hydrogen bromide, or hydrogen iodide adducts of hydroxylamines. Also important is the absence of significant concentrations of potentially interfering components in breath, of either healthy or metabolically stressed individuals. This reaction is quite specific to ketones and aldehydes.

Figure 2:
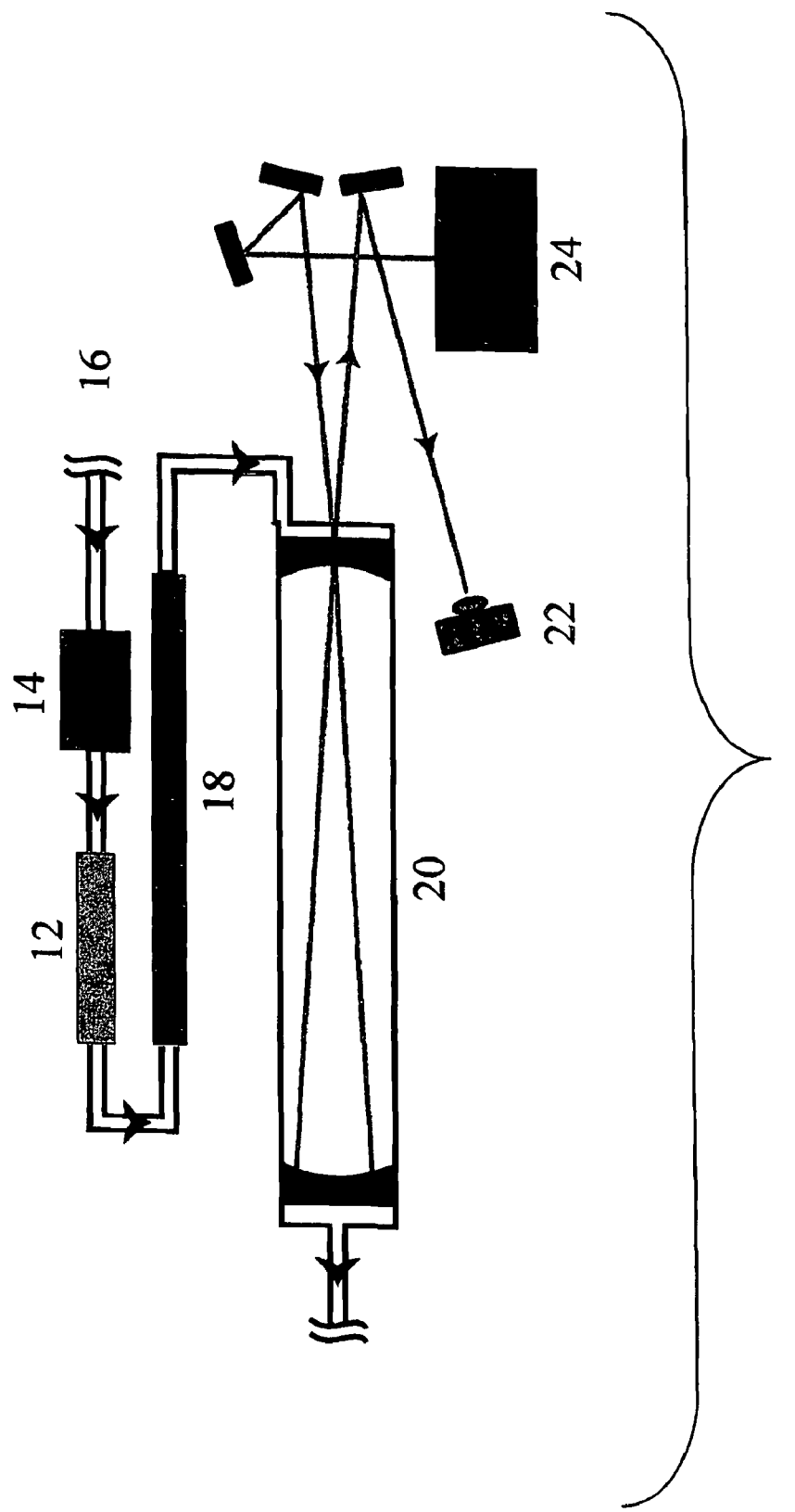
FIG. 2 is a diagram of the preferred ketone/aldehyde vapor sensor of the invention.

The invention is also of a diode laser based, non-invasive, breath acetone sensor capable of detecting the early onset of ketosis. A preferred embodiment of sensor 10 is shown in FIG. 2, comprising desiccant 12, sample pump 14, inlet for breath (air) sample 16, reactor tube 18, optical cell 20, detector 22, and laser 24. A breath sample is first dried by passage over a deliquescent desiccant such as $CaCl_2$. Then, the dry breath sample is passed through a column of a hydroxylamine hydrochloride (the reactor) where acetone reacts to produce an amount of HCl gas proportional to the acetone concentration. The gaseous output of the reactor is then directed to an optical cell where the HCl is quantified using diode laser spectroscopy. Knowledge of the acetone to HCl conversion efficiency determined using an acetone standard of known concentration allows the calculation of the breath acetone concentration. Thereby, the breath acetone (BA) is related to the measured HCl concentration by the relation BA (ppm) =HCl(ppm)/(fractional conversion efficiency).

Figure 3:
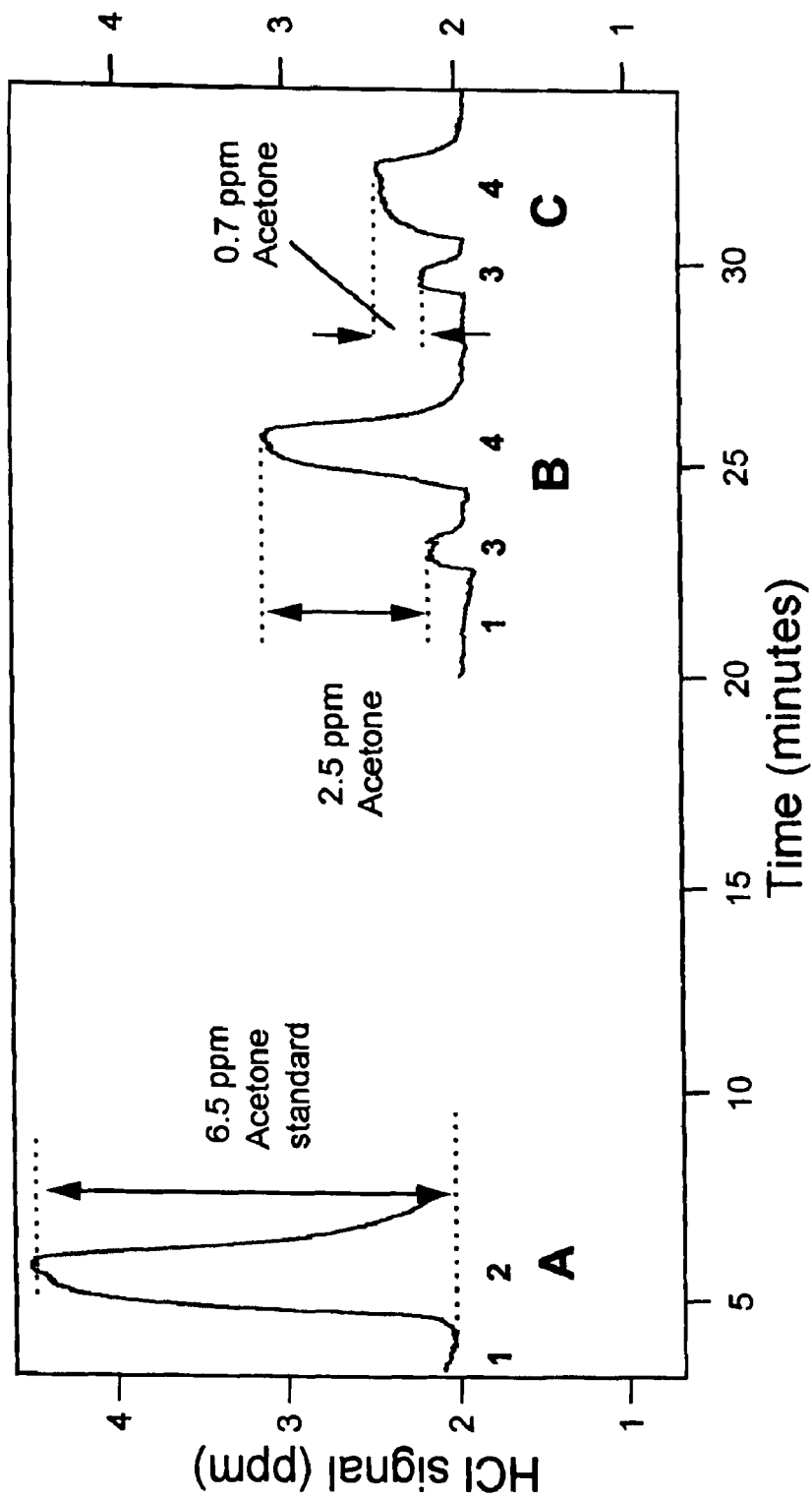
FIG. 3 shows sensor response (ppm HCl) for a 6.5 ppm acetone in nitrogen standard, and two breath samples.

Some hydroxylamine hydrochlorides are reactive to oxygen. For these hydroxylamine hydrochlorides, a baseline HCl response due to the oxygen content of expired breath can be calculated. Expired breath contains less oxygen than ambient air and the oxygen content of breath varies significantly for individuals. A preferred method of determining the baseline HCl response due to the breath oxygen is to remove the acetone from the breath sample by trapping on a desiccant that traps acetone as well as water, e.g., calcium sulfate or type 3A molecular sieves. FIG. 3 shows the HCl concentration profile for an acetone conversion efficiency calibration and two breath acetone measurements. During the course of the measurement, gas is changed between nitrogen (1), breath is passed through a desiccant (3), and breath is passed through another desiccant, which does not trap acetone (4). A 38 percent acetone to HCl conversion efficiency for reactor tube 18 was determined from sensor response to a 6.5 ppm acetone standard (A2). The results of the breath measurement indicate acetone concentrations of 2.5 ppm and 0.7 ppm for subjects B and C. Subject B fasted for 17 hours and recorded a slightly high breath acetone value.

FIG. 3 shows a small sensitivity to oxygen—peaks B3 and C3—corresponding to approximately 0.5 ppm acetone. Variations in exhaled oxygen concentrations will produce varying offsets. For diabetic screening applications, where breath acetone concentrations exceed 5 ppm, the oxygen induced signal can be treated as a fixed offset that is small compared to target values. For more accurate measurements, part of the breath sample is flowed through a first desiccant to remove both acetone and water, leaving exhaled oxygen as the only HCl generating species (B3 and C3 in FIG. 3). Then the flow is switched to a second desiccant that removes water and passes acetone. The resulting HCl increase is due exclusively to acetone (B4 and C4 in FIG. 3).

The measurements in FIG. 3 were made using a nitrogen gas flow (A1, B1 and C1) as a baseline. The oxygen to HCl conversion efficiency of reactor 14 was low, typically 0.0002 to 0.0003 percent. The oxygen reactivity complicated the breath acetone measurement slightly.

Breath measurement can be made without a nitrogen source, against an air background. In this preferred embodiment, the breath oxygen baseline B3 and C3 is lower than air background. When sensor 10 is optimized properly, the acetone sensitivity is conservatively estimated at several tenths of a ppm, and is appropriate for breath acetone measurements of healthy, metabolically stressed, and diseased individuals.

A preferred breath acetone measurement procedure as illustrated in FIG. 3 is as follows:

1. Calibration of reactor tube 18 using a calcium chloride desiccant to determine the acetone to HCl conversion efficiency (CE), represented by A in FIG. 3.

2. Measurement of the baseline HCl response to oxygen (O) of the breath sample by inserting a second desiccant (calcium sulfate) that traps acetone from the breath sample flow prior to reactor tube 18, represented by B3 and C3 in FIG. 3.

3. Removal of the calcium sulfate desiccant leaving only a $CaCl_2$ desiccant and measuring the full HCl response (A+O) to both acetone and oxygen, represented by B4 and C4 in FIG. 3.

4. The breath acetone concentration can then be calculated using the expression $\{(A+O)-(O)\}/(CE)$, where A, O are in parts per million.

For hydroxylamine hydrochlorides that have negligible oxygen reactivity, step 2 can be omitted and a baseline HCl response for ambient air employed.

This hydroxylamine (HA) chemical reaction to produce HCl has a linear response to acetone concentration. The apparatus of the invention shows adequate sensitivity and achieves minimum detectable acetone concentrations of <1 ppm. This performance guarantees excellent signal-to-noise ratios for identification of ketoacidotic and diabetic people. Table 1 lists breath acetone concentrations for both healthy and diseased humans.

TABLE 1

Human Acetone Levels

| Physical State | Blood Acetone Concentration (mg/liter) | Breath Acetone Concentration (mg/liter) | (ppm) |
|---|---|---|---|
| Healthy | 0.843 | 1.164 to 1.35 | 0.5 |
| 3-Day Fasted | 46.56 | 64.6* | 27* |
| Ketoacidotic | 2906 | 403* | 170* |
| | 4244 | 589* | 248* |
| Diabetic** | | | 2 to 5** |

*calculated using 720:1 blood to breath acetone ratio from healthy values.
**insulin-dependent, adequately controlled.

The sensor of the present invention preferably uses a chemisorbent solid material (most preferably hydroxylamine hydrochloride) to both trap and react with acetone. The gas-solid reaction of acetone releases gaseous HCl in proportion to the concentration of acetone. Real time, diode laser measurement of the concentration of the HCl gas generated precisely quantifies the amount of breath acetone with a much higher sensitivity and larger dynamic range than is possible with colorimetric techniques such as used in Draeger tube technology. In sensor 10, the breath sample preferably passes through a reactor bed of a hydroxylamine hydrochloride and the resulting HCl gas concentration is measured by wavelength modulated diode laser spectrometry in the following optical cell.

The preferred breath acetone sensor of the invention combines two technologies: 1) the gas-solid reaction of acetone in exhaled air with a hydroxylamine hydrochloride, modified or unmodified, and 2) the quantitative measurement of the reaction product, HCl, using diode laser spectroscopy. The first step—the acetone to HCl conversion—is related to a recently developed method for determining acetone in workplace air. That method, however, uses gas chromatographic analysis of the oxime product. "A New Passive Sampler for Aldehydes", Tsai, S. -W. and S. S. Q. Hee, American Industrial Hygiene Association Journal, 2000. 60: p. 463-473; and "A New Passive Sampler for Regulated Workplace Ketones", Tsai, S. -W. and S. S. Q. Hee, American Industrial Hygiene Association Journal, 2000. 61: p. 808-814. The present approach is much less cumbersome (faster and portable) because one detects the HCl directly.

The HCl detection system of the invention preferably uses optical spectroscopy with a near-infrared diode laser. This gas phase, non-contacting measurement technique is sensitive, highly selective, fast, linear, and free of hysterisis. The laser preferably accesses an overtone vibrational transition in HCl at 1742.4 nm instead of the fundamental band at 3500 nm. The overtone band is weaker, but wavelength modulation techniques provide adequate sensitivity for the ketosis monitor. In contrast, laser sources able to access the fundamental band require cryogenic cooling and/or high power electronics as well as expensive, cooled detectors. The advantages of working with near-infrared lasers far outweigh the difference in sensitivity.

Figure 4:
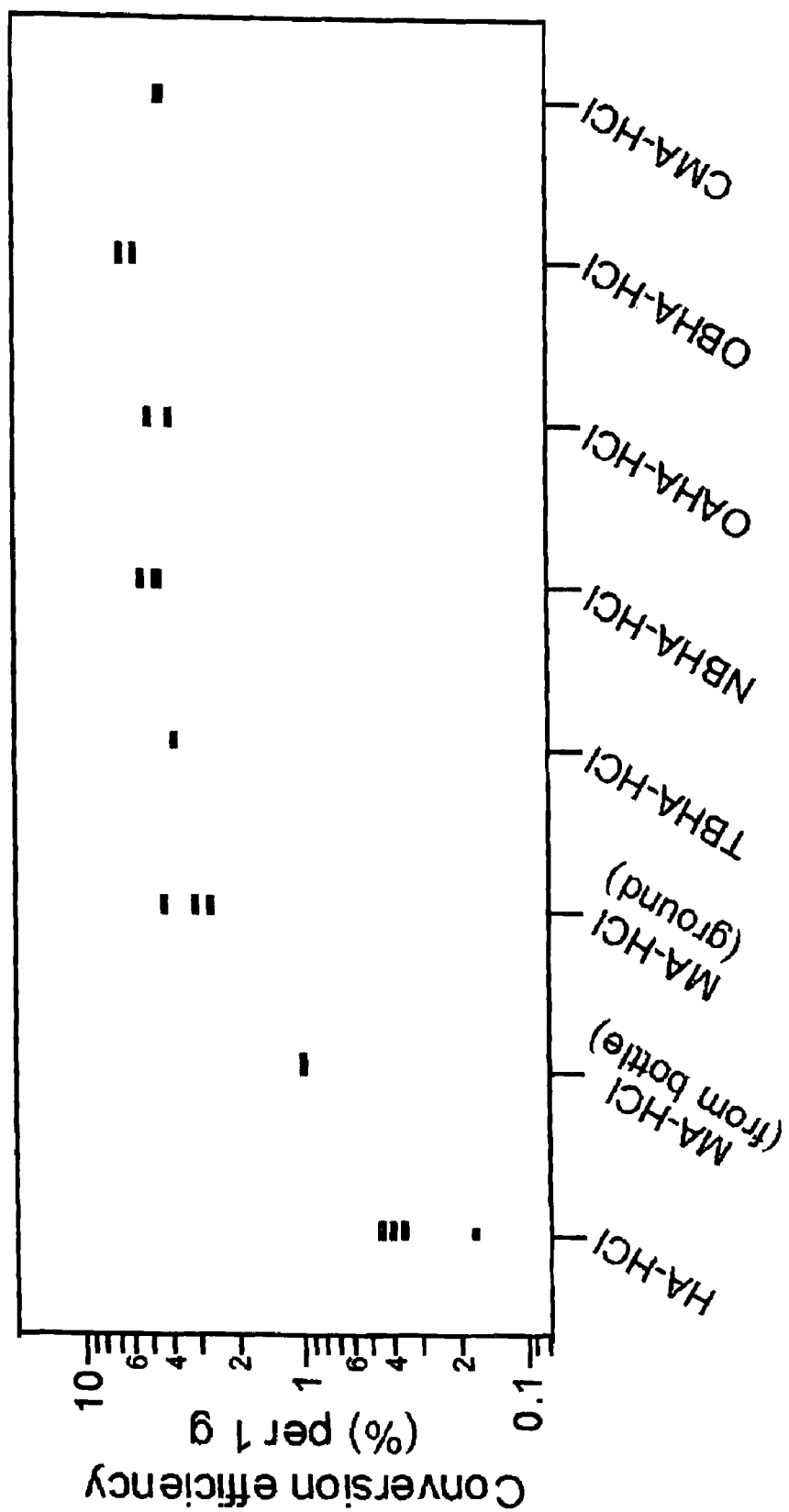
FIG. 4 is a plot of the acetone to HCl conversion efficiencies for various hydroxylamine hydrochlorides presented in percent conversion per gram.

A survey was conducted of hydroxylamine hydrochlorides to identify many commercially available modified hydroxylamine hydrochlorides. Rather than describing each material the acetone to HCl conversion efficiencies of hydroxylamines are summarized in FIG. 4. Hydrochloride salts of hydroxylamine (HA), methoxylamine (MA), finely ground methoxylamine (MA_fine), t-butylhydroxylamine (TBHA), O-(4-nitrobenzylhydroxylamine) (NBHA), O-allyl hydroxylamine (OAHA), O-benzylhydroxylamine (OBHA), and carboxymethoxylamine (CMA) were tested.

The acetone to HCl conversion efficiencies are expressed per gram material to provide comparison of test runs using 1 to 4.5 grams of hydroxylamine. One sees 30 to 50 percent conversions for OBHA reactors. The reactors may be heated to increase the conversion efficiency, however this is not required. For the data presented in FIG. 5, a 25 ppm acetone sample was flowed at 250 ml/min through the reactors. Of the hydroxylamines tested, it is presently preferred to use OBHA hydrochloride and MA hydrochloride in the breath sensor due to its consistent powder quality, availability, and pricing.

Experiments were conducted to show that the acetone measurement technique is unlikely to exhibit false positives and that typical background gases do not interfere with the acetone measurement.

Acetaldehyde. Hydroxylamine hydrochloride, either unmodified or modified to pentafluorobenylhydroxylamine (PFBHA) or MA-HCl, is reactive to most aldehydes and ketones. The possibility of other trace breath gases giving rise to HCl measurements must be considered. The other common ketone bodies of human metabolism, acetoacetate and betahydroxybutyrate, are ionic compounds at physiological conditions and will not have appreciable vapor pressure. Instead, the two likely interferences are formaldehyde and acetaldehyde. Formaldehyde is not produced in human metabolism with the sole exception of methanol ingestion. This is a very uncommon case that should not affect the utility of the proposed sensor. However, acetaldehyde can occur in breath from the metabolism of ethanol, albeit at much lower levels than are important for diagnosis of irregular metabolism by acetone detection.

Acetaldehyde experiments were performed under identical conditions as those for acetone. A 159 ppm sample of acetaldehyde in nitrogen was prepared on the vacuum line by a series of dilutions starting with pure acetaldehyde vapor from the liquid. The pentafluorobenzyl modified hydroxylamine hydrochloride (PFBHA-HCl) was tested first. Although the studies of chemisorbent air samplers ("Sampling and Determination of Formaldehyde Using Solid Phase Microextraction with On-Fiber Derivitization," P. A. Martos, J. Pawliszyn, Analytical Chemistry, 1998, 70: p. 2311-2320; and "Field Sampling and Determination of Formaldehyde in Indoor Air with Solid Phase Microextraction and On-Fiber Derivitization," J. A. Koziel, J. Noah, J. Pawliszyn, Environmental Science and Technology, 2001, 35: p. 1481-1486) do not indicate increased reactivity of acetaldehyde with PFBHA-HCl over that of ketones, the results show that acetaldehyde is 2.5 times more reactive than acetone. An acetaldehyde to HCl conversion efficiency of 14.2 percent was also measured for MA-HCl compared with 6.2 percent for acetone.

The increase in reactivity of acetaldehyde above that of acetone, measured for both PFBHA-HCl and MA-HCl, would result in a worst case, false positive reading of 0.2 ppm acetone for someone with a blood alcohol content of 0.16% (twice the legal driving limit in most states). This is a measurable error for the ketosis sensor's lowest target acetone concentration of 1 ppm for a healthy individual but is small compared to concentrations of >100 ppm diagnostic of ketotic individuals or poorly maintained diabetics.

Ethanol. When a 185 ppm ethanol vapor sample passed through the MA-HCl reactor, it did not result in HCl signals above the background.

Carbon Dioxide. Ambient $CO_2$ concentration in air is 350 ppm and breath $CO_2$ concentrations can range from several thousand ppm and above depending upon level of exercise. Carbon dioxide is not expected to affect the conversion of acetone to HCl by the chemisorbent solid, thus mixtures of acetone and $CO_2$ were not tested. Rather the question addressed by the experiments is the reactivity of $CO_2$ with the chemisorbent solid and subsequent generation of HCl. A sample vapor stream of 1 percent $CO_2$ in nitrogen was tested and no HCl was observed after flowing through the reactor containing MA-HCl. Thus, it can be confidently stated that carbon dioxide at percent levels and higher will not interfere with the method of the invention.

Water. Exhaled breath is saturated with water at roughly six percent for a body temperature of 37° C. This could result in condensation of water on the optics of the HCl detection system that could be prevented either by heating the reactor and optical cell above 37° C. or removing water from the breath sample by a hygroscopic solid.

Hydroxylamine hydrochlorides were deposited onto various solid supports and recorded similar acetone to gaseous HCl conversions. The solid support materials used include cellulose acetate fiber, cellulose acetate filter blanks (cigarette filters), glass beads (treated and untreated), fluorosil (chromatographic support), and polypropylene yarn.

Deposition of hydroxylamine hydrochlorides has been accomplished by solvent removal of hydroxylamine-HCl solutions and by sublimation of the hydroxylamine-HCl directly to the solid support. Many hydroxylamine hydrochlorides sublimate with the hydrogen halide group attached. Elemental analysis results confirm this observation. The reactivity of pure powders of hydroxylamine hydrochlorides can be enhanced by sublimation prior to packing in the reactor.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of quantifying ketone or aldehyde concentrations in a gas, the method comprising the steps of:
    passing the gas sample through a reactor comprising a solid hydroxylamine hydrogen halide material that reacts with ketones or aldehydes and flowing the gaseous reaction product of the ketone or aldehyde comprising a hydrogen halide into an optical cell;
    employing spectroscopy of the gaseous reaction product in the optical cell to determine a hydrogen halide concentration of the gaseous reaction product of the ketone or aldehyde; and
    calculating the ketone or aldehyde concentration from the hydrogen halide concentration of the gaseous reaction product and a predetermined reaction conversion efficiency.

2. The method of claim 1 additionally comprising the step of passing the gas sample through a desiccant.

3. The method of claim 1 wherein the ketone or aldehyde comprises acetone.

4. The method of claim 1 wherein the ketone or aldehyde comprises formaldehyde.

5. The method of claim 1 herein the hydroxylamine hydrogen halide material comprises one or more hydroxylamine hydrogen halides selected from the group consisting of hydrogen halide adducts of hydroxylamine (HA) and modified HA materials with oxygen bound substituents.

6. The method of claim 1 wherein the hydroxylamine hydrogen halide material comprises one or more hydroxylamine hydrogen halides selected from the group consisting of hydrogen halide adducts of hydroxylamine (HA) and modified HA materials with nitrogen bound substituents.

7. The method of claim 1 additionally comprising the step of determining the conversion efficiency by initially measuring the gaseous reaction product concentration of an acetone sample of known concentration.

8. The method of claim 1 additionally comprising the step of determining the correction for the sample oxygen content by employing a second desiccant.

9. The method of claim 8 wherein the second desiccant comprises calcium sulfate.

10. The method of claim 1 wherein the employing step comprises employing diode laser spectroscopy.

11. The method of claim 10 wherein the employing step detects HCl at an overtone vibrational transition.

12. The method of claim 11 wherein the employing step detects HCl at approximately 1742.4 nm.

13. The method of claim 1 wherein the method is employed to test for one or more of the items selected from the group consisting of diabetes screening, diabetes maintenance, identification and quantification of ketosis, explosives detection, and formaldehyde detection.

14. The method of claim 1 wherein the hydrogen halide comprises HCl.

* * * * *